United States Patent [19]

Costanza: John R. et al.

[11] Patent Number: 4,623,540

[45] Date of Patent: Nov. 18, 1986

[54] CONTROLLED RELEASE INSECTICIDE COMPOSITION

[75] Inventors: Costanza: John R., N. Plainfield, N.J.; Henry A. Terwedow, Glen Ellyn, Ill.

[73] Assignee: Les Produits Organiques du Santerre-Orsan S.A. ("Orsan"), France

[21] Appl. No.: 281,818

[22] Filed: Jul. 9, 1981

[51] Int. Cl.[4] ............................................. A01N 57/00
[52] U.S. Cl. ........................................ 424/81; 514/80
[58] Field of Search ...................... 424/81, 200; 514/80

[56] References Cited

U.S. PATENT DOCUMENTS

| | | | |
|---|---|---|---|
| 2,767,194 | 10/1956 | Fancher | 260/402.5 |
| 3,212,967 | 10/1965 | McFadden et al. | 424/81 |
| 3,592,910 | 7/1971 | Clark et al. | 424/81 |
| 3,743,728 | 7/1973 | Fancher | 424/200 |
| 3,959,237 | 5/1976 | Blank | 424/81 |
| 4,145,439 | 3/1979 | Schulze et al. | 424/330 |
| 4,174,445 | 11/1979 | Möhring et al. | 424/249 |
| 4,220,663 | 9/1980 | Schulze et al. | 424/330 |
| 4,263,287 | 4/1981 | Dennis | 424/200 |
| 4,282,207 | 8/1981 | Young et al. | 424/81 |
| 4,282,209 | 8/1981 | Tocker | 424/81 |
| 4,343,790 | 8/1982 | Pasarela | 424/202 |

*Primary Examiner*—Albert T. Meyers
*Assistant Examiner*—John M. Kilcoyne
*Attorney, Agent, or Firm*—Scully, Scott, Murphy & Presser

[57] ABSTRACT

An emulsifiable concentrate of Imidan, an acrylic or styrene resin, a surfactant and an aliphatic organic solvent functions as a controlled release insecticide when applied to plant foliage. The organic solvent is a solvent for the resin and the surfactant but is a non-solvent for the Imidan.

9 Claims, No Drawings

CONTROLLED RELEASE INSECTICIDE COMPOSITION

BACKGROUND OF THE INVENTION

1. Field of the Invention

This invention relates to an insecticide composition. More particularly it relates to a controlled release foliar insecticide composition. This invention especially relates to a controlled release composition containing an organo-thiophosphate insecticide, Imidan.

2. Description of the Prior Art

Foliar insecticides can be broadly classified by the manner in which they provide effective control. Some insecticides are toxic as contact poisons, e.g., they are lethal to insects by being brought in contact therewith as when an insect lights onto or crawls on foliage coated with the insecticide. Others prove lethal to insects as a stomach poison when the insect ingests insecticide-coated foliage.

The farmer's goal is to realize the highest possible return on his investment. Therefore, maximizing the yield of the marketable commodity is of prime concern. Apart from the proper use of fertilizers, adapted varieties and proper cultural practices, the farmer depends on crop protection chemicals to maximize yield. While the rationale for their use against weeds, diseases and insects is obvious, there are a number of associated disadvantages. These include such factors as toxicity, residuality, cost, resistance by pests, and weatherability. These factors are somewhat interrelated and in recent years, attempts have been made to deal with them.

Improving the efficiency of foliar insecticides can be achieved by reducing the application rates or by reducing the number of applications. The classical objective of controlled release technology is to extend the longevity of a pesticide thereby leading to decreased use and increased benefit to both the farmer and the consumer. Controlled release of a foliar insecticide is one effective means of reducing the per acre cost of the insecticide. Not only are the number of applications reduced but effectiveness of the insecticide is increased and undesirable side-effects to beneficial-insects often minimized through reduced run-off and reduced spray drift.

Although the field of controlled release technology has been practiced for a number of years in the pharmaceutical industry, it is only recently that active interest has been displayed in the use of this technology for agricultural pesticides.

In one application, an interfacially polymerized microcapsule product containing methyl parathion has been utilized on cotton plants. In another, a laminate containing pesticide sandwiched between layers of plastic film has been applied to agricultural systems. (Proceedings of the Controlled Release Pesticide Symposium (1976).)

U.S. Pat, No. 3,212,967 to McFadden et al. discloses biocidally-active phosphorothioate esters which are polymerized with ethenoid monomers, such as acrylates, methacrylates and the like to form unitary polymeric molecules having the biocidal component temporarily held therein. The biocidal component is slowly released from the polymeric material in which it is entrapped when the materials are employed as film-forming coatings. These biocidally-active organic, polymeric materials are applied as aqueous latex dispersions or organic solvent solutions.

U.S. Pat. No. 3,592,910 to Clark et al. is directed to the use of liquid polyterpenes to protect pesticides against weathering and to extend the residual life of the pesticide. Pesticides, including insecticides, are controlled by release from these formulations. The polyterpene-containing composition may be applied to plants in undiluted condition, as a water emulsion or an organic solvent solution. This patent also states that acrylic polymers, vinyl-acrylic copolymers and other resins have been used as sticking agents for pesticides. However, no improved biological efficacy was reported for any of these compositions.

U.S. Pat. No. 2,767,194 to Fancher discloses a number of monothio- and dithio-phosphates and their method of preparation. These products are useful as insecticides and acaracides. One particularly effective dithio-phosphate is N-(mercaptomethyl) phthalimide-S-(O,O-dimethyl phosphorodithioate) which is also known as Imidan. These compounds were effective when acetone solutions thereof were dispersed in water with surfactants and applied as a spray.

Imidan is primarily used for the control of insects that attack commerical farm crops, especially fruit crops. The insects which are effectively controlled by Imidan include alfalfa weevil, apple maggot, coddling moth, grape berrymoth, green apple aphid, Mexican bean beetle, oriental fruit moth, plum curculio, redbanded leafroller, rosy aphid, tobacco hornworm and tobacco budworm. The commercial cash crops treated with Imidan include such fruit crops as apples, apricots, cherries, grapes, nectarines, peaches, pears, plums and strawberries, as well as alfalfa, almonds, beans, citrus, corn, peas, pecans, potatoes, tobacco, rice and the like. Sales of Imidan in 1976 for use on apple orchards alone constituted over two million dollars and amounted to over four million dollars for use on all fruit crops.

Imidan is a white crystalline solid and is available commercially in technical grade purity of 94–96%. (All percentage figures herein are in terms of weight unless stated otherwise.) It is also available as a 50% active wettable powder. Imidan has been applied to cash crops as a foliar insecticide in the form of an aqueous spray. In this form, the adhesion to leaf surfaces, particularly if they are dirty or dusty, is not good and the weathering from rainfall requires repeated applications.

It has been discovered and disclosed in related patent application Ser. No. 358,125 that a controlled release insecticide composition can be prepared in the form of an emulsifiable concentrate which contains Imidan, an acrylic resin, a surfactant and an organic solvent in which all of the ingredients are soluble. By employing the Imidan in its technical grades or in its pure crystalline form, this composrtion is insecticidal to foliage eating or chewing insects susceptible to stomach poisons while leaving insects susceptible to contact poisons essentially unaffected.

It is an object of the invention to increase the efficacy of Imidan by increasing its retention on leaf surfaces and increasing its weatherability, specifically against rainfall stress.

It is another object of this invention to provide Imidan in a controlled release formulation.

It is still another object of this invention to provide Imidan in a manner which reduces the frequency of application.

It is still a further object of this invention to provide a means of applying Imidan to foliar substrates whereby the runoff of the insecticide to the surrounding environment is substantially reduced.

SUMMARY OF THE INVENTION

In accordance with the present invention it has been found that Imidan can be provided as an emulsifiable concentrate in a controlled release insecticide composition and that when applied to foliar substrates it is at least as efficacious and usually more efficacious than the conventional aqueous spray of wettable powder Imidan as either a contact poison or a stomach poison insecticide both before and after rainfall.

More particularly, this invention is directed to a controlled release insecticide composition comprising:

(a) an insecticidal effective amount of Imidan, (b) an amount of acrylic or styrene resin effective to controllably release said Imidan, (c) a surfactant, and (d) an aliphatic organic solvent in which the resin and the surfactant are substantially soluble but the Imidan is substantially insoluble.

This invention is also directed to a method of controlling foliage eating or chewing insects susceptible to stomach poisons and insects susceptible to contact poisons which comprises applying the Imidan compositions of this invention to foliar substrates.

DESCRIPTION OF THE PREFERRED EMBODIMENTS

This invention relates to a controlled release formulation containing Imidan, an acrylic or a styrene resin, a surfactant and an aliphatic organic solvent which is a solvent for the resin and the surfactant but a nonsolvent for the Imidan.

N-(mercaptomethyl)-phthalimide-S-(O,O-dimethyl phosphorodithioate) is a foliar insecticide. It is known as Imidan and also as Phosmet, Prolate and Appa. It will be referred to herein as Imidan. Imidan has the following structural formula:

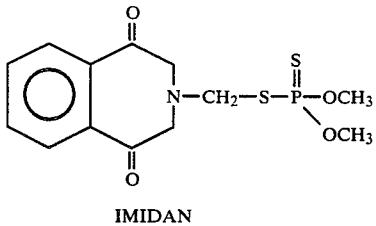

IMIDAN

Imidan is a white crystalline powder and is available commercially as a technical grade product (94–96% purity) or as a wettable powder formulation (50% active ingredient).

The Imidan formulations of this invention consist of Imidan (usually in the form of a wettable powder) dispersed in a nonaqueous system containing polymer, solvent, and surfactant. An important element of this invention is that the solvent or solvent combination must be a nonsolvent for the insecticide, but a solvent for the polymer. This unique combination of materials results in compositions that are unexpectedly more effective than the conventional wettable powder insecticide. Wettable powder insecticides are technical grade pesticides that are adsorbed on particulate substrates such as clay or other minerals. The significantly improved properties obtained by using the compositions of this invention are: dual-mode insecticide action, stability against settling, more uniform application rate, better distribution on plant surfaces, greater adhesion to plants, diffusion-controlled insecticide release rate, increased weather resistance, improved efficacy against insects, and longer periods of activity.

The dual-mode of insecticidal activity of these compositions results in their being effective against insects by acting as either contact or stomach poisons. They are easily dispersed in water prior to application because the surfactant present helps to bridge the water: Imidan composition interphase. In addition, these compositions are stabilized against settling when dispersed in water by the surfactant bridge between phases.

When applied by conventional spraying techniques, a more uniform application to foliage results because these Imidan compositions are easily and homogeneously dispersed in water. Greater adhesion to plants and trees occurs because the hydrophobic droplets that form when these compositions are dispersed in water readily deform upon impact (being liquid) and wet the hydrophobic foliage when sprayed.

The Imidan compositions of this invention are more effective for longer periods of time, and have increased weather resistance because the active insecticide is released by a diffusion controlled release rate. Diffusion controlled release results as a consequence of the polymer film that the pesticide is dispersed in after the composition is applied to the leaf surface. The polymer film reduces insecticide loss by evaporation or weather erosion thereby increasing insecticidal efficacy. Conventional wettable powder insecticides are easily lost by volatilization, abrasion, and weathering, thus reducing their utility.

The acrylic resins which can be used herein can be selected from among the polymers and copolymers derived from the polymerization of alkyl acrylate monomer, alone or together with one or more other monomers copolymerizable therewith. The alkyl acrylate monomer is derived from the reaction of a monohydric alcohol, preferably of from 6 to about 18 carbon atoms, and more preferably, from 6 to 10 carbon atoms, with acrylic acid. Among the alkyl acrylates which are useful herein are included hexyl acrylate, octyl acrylate, decyl acrylate, dodecyl acrylate, 2-ethylhexyl acrylate, and the like. The foregoing monomers and mixtures thereof can be polymerized in accordance with known and conventional procedures and, as previously stated, can be interpolymerized with other copolymerizable monomers including alpha olefins such as ethylene, propylene or butylene; vinyl esters such as vinyl formate, vinyl acetate and vinyl butyrate; acrylamides and alkyl acrylamides such as methyl acrylamide, ethyl acrylamide and methyl methacrylamide; vinyl ethers such as methyl vinyl ether and t-butyl vinyl ether; vinyl ketones such as methyl vinyl ketone; dicarbonates such as diethyl fumarate and diethyl maleate; acid anhydrides such as maleic anhydride; and, styrene. Preferred copolymers include vinyl acetate/2-ethylhexyl acrylate and styrene/2-ethylhexyl acrylate. The percentage of acrylic/acrylate monomer(s) by weight which can be incorporated into useful acrylic resins according to this invention, can vary over a wide range and in general will range from a minimum of about 30% up to 100% of the weight of the polymer.

The styrene resins which can be used herein are usually a styrene homopolymer although styrene can be employed as one of the monomers in the useful acrylic copolymer resins described above. Styrene can be polymerized in accordance with known and conventional procedures such as mass polymerizations, suspension polymerization, solution polymerization or a combination of these procedures.

Typically, the resins will be incorporated into the insecticide emulsifiable concentrates employing an organic solvent which is a solvent for the resin and the surfactant but a non-solvent for the Imidan. Thus, the organic solvent is conventionally an aliphatic organic solvent in which the resin and the surfactant are substantially soluble and the Imidan is substantially insoluble. Among the useful organic solvents are the normally liquid aliphatic hydrocarbons such as hexane, heptane, octane and the like as well as mixtures thereof. Particularly useful are such commercially available solvents as mineral spirits, Kwik-Dri and kerosene. Mineral spirits is a petroleum-derived solvent containing little or no aromatic solvent Kwik-Dri is a tradename for an aliphatic petroleum naphtha containing essentially no aromatic compounds. Kerosene is also petroleum-derived and contains little, if any, aromatic solvents. Combinations of these solvents may also be employed, particularly where the resin or the surfactant is insoluble or exhibits limited solubility in a single solvent.

A broad variety of surfactants can be employed with this invention. These surfactants aid in the emulsification of the compositions when they are added to water by providing adequate dispersion. They also provide enhanced wetting and sticking action so that the insecticide composition more readily adheres to the foliage of the plants. Suitable surfactants may be selected from the anionic, cationic, and nonionic types including primary, secondary and tertiary alkyl amines, ethoxylated alcohol sulfates, alkyl sulfates, water soluble salts of a sulfonated alkyl, alkylbenezene, or alkyl glycerol ether, quaternary ammonium salts, quaternary imidiazolinium salts, alkyl pyridinium salts, dialkyl morpholinium salts, ethyoxylated fatty acids, sorbitol esters, alkylphenoxypoly (ethyleneoxy) ethanols, aromatic sulfonate-oxide condensates and the like. Preferred are the "Agrimuls" (Diamond Shamrock Corp.) which are a blend of anionic and nonionic aromatic sulfonate-oxide condensates and the "Igepals" (GAF Corporation) which are alkylphenoxypoly (ethyleneoxy) ethanols.

Fairly wide latitude in proportioning the amounts of Imidan insecticide, resin, solvent and surfactant in the emulsifiable concentrates of this invention is permissible. The amount of Imidan must, of course, be sufficient to provide an insecticidal effective amount when the composition of the invention, diluted with water in its usual form of application, is applied to a foliar substrate. This amount will be dependent on the nature of the insects encountered, the degree of infestation and the nature of the plants to be treated. Regarding the acrylic or styrene resin, the amount present in the emulsifiable concentrates must be effective to controllably release the Imidan when the composition of the invention is in place on the plant foliage. In general, the Imidan insecticide can be present in an amount of from about 0.1 to about 50 percent by weight and preferably from about 1 to about 40 percent by weight. The acrylic or styrene resin can be incorporated in the concentrates so as to represent from about 0.5 to about 50 percent, and preferably from about 1 to about 30 percent, of the weight of the concentrate. The amount of solvent employed will depend primarily on the solvency of the particular solvent(s) selected for the particular resin and the particular surfactant, it being desired that there be essentially complete dissolution of the resin and the surfactant in the solvent of choice. Typically, from 1:1 to 10:1 weight parts of solvent per weight parts of resin can be employed. With respect to surfactant, good results can be obtained using this component at from about 1 to about 10 percent be weight of the concentrate.

Although there is no criticality with respect to the sequence in which the aforesaid components are combined to prepare the concentrates, the resin will usually be dissolved in the solvent (unless the solvent was also used as the reaction medium in which the resin was prepared) and the resin solution will thereafter be mixed with the remaining ingredients.

The following examples illustrate embodiments of this invention.

In evaluating test formulations of the Imidan compositions, several bioassay procedures were utilized. These are described below:

A. Tobacco Budworm (*Heliothis virescens*)

Bioassaying with tobacco budworms was conducted at an outside facility. Second instar larvae reared on a Shorey pinto bean diet in that laboratory served as the test organisms.

Young greenhouse cotton in the two leaf stage was sprayed to run off with the various formulations and air dried. Rainfall was applied by a rainfall simulator. Plants left on this machine for 1 hr. received the equivalent of one inch of rainfall. The cotton was again air dried and subsequently tested with 5 tobacco budworm larvae per treatment. After 48 hours the insects were examined for mortality or morbidity.

B. Mexican Bean Beetle (*Epilachna varivestis*)

A strain of Mexican bean beetle obtained from Boyce Thompson Institute, (BTI), Yonkers, N.Y. was maintained in colony. Both adults and larvae were reared solely on mammoth podded horticultural pole beans. This same variety of bean, 8 days post-planted, was used in the bioassay. Both the spraying and raining procedure are similar to that described in the tobacco budworm bioassay. After drying, the plants were cut at the stem and tested. The sprayed bean cutting was placed in an 8-oz.Dixie cup. The stem protruded through a small hole in the bottom of the cup into a petri dish of water. Five beetle larvae were added to each plant and allowed to feed for 72 hr., after which mortality was scored.

C. Housefly (*Musca domestica*)

A colony of the USDA-Beltsville strain of houseflies was established. Immature flies were reared entirely on CSMA medium (Ralston Purina). A powdered milk and confectionary sugar mixture was the nutritional source for the adults. Only 24–72 hr. post-emerged adults were used for testing.

McIntosh apples provided the substrate in this bioassay. The apples were sprayed to runoff as described above and placed in a ½ gallon cardboard cylinder. Thereafter, twenty-five houseflies were introduced into the container and mortality was scored after 72 hours.

EXAMPLE I

A typical acrylic resin used in this invention, a polymer of vinyl acetate and 2-ethylhexyl acrylate, was prepared from the following ingredients:

|  | Wt. % |
|---|---|
| Vinyl acetate | 22.5 |
| 2-Ethylhexyl acrylate | 22.5 |
| Xylene | 45.0 |
| Ethyl acetate | 9.0 |
| CBenzoyl peroxide | 1.0 |

The polymer was prepared as follows:

The two monomers and the xylene solvent were mixed together to form Fraction A. The benzoyl peroxide was dissolved in the ethyl acetate and identified as Fraction B.

300 ml of Fraction A and 40 ml of Fraction B were placed in a 2 liter flask equipped with a reflux condenser and a stirrer. The contents of the flask were heated under reflux for a period of 1½ hours during which additional quantities of Fraction A and Fraction B were added to the flask. Heating under reflux was continued for an additional 3-4 hours. The contents of the flask constituted a solution of vinyl acetate/2-ethylhexyl acrylate polymer.

In a similar fashion other polymer solutions were prepared from these and other monomers including styrene.

Formulations of the present invention, having the compositions shown in Table I were prepared as emulsifiable concentrates as follows:

The resin and the surfactant were dissolved in the solvent. Then the Imidan was added and the mixture was tumbled overnight to prepare the liquid concentrates.

TABLE I

COMPOSITION OF IMIDAN COMPOSITIONS

| | Grams of Components Sample No. | | | |
|---|---|---|---|---|
| | 1 | 2 | 3 | 4 |
| Polymer | | | | |
| VAc/2-EHA[1] Copolymer | 7.20 | 7.20 | 7.20 | 7.20 |
| Surfactant | | | | |
| Igepal CO-630 | 0.60 | 1.20 | | |
| Igepal CO-850 | | | 0.60 | 1.20 |
| Solvent | | | | |
| Heptane | 8.00 | 8.00 | 8.00 | 8.00 |
| Insecticide | | | | |
| Imidan 50 WP | 9.82 | 9.64 | 9.64 | 9.64 |

[1]VAc = Vinyl Acetate; 2-EHA = 2-ethylhexyl acrylate

These compositions and Imidan 50 WP were diluted in water to a 400 ppm Imidan concentration and evaluated in the housefly bioassay. The results are presented in Table II below.

TABLE II

BIOASSAY OF IMIDAN COMPOSITIONS AGAINST HOUSEFLIES (400 PPM)

| SAMPLE IDENTIFICATION | PERCENT HOUSEFLY MORTALITY ON APPLES | | |
|---|---|---|---|
| | 24 Hrs. | 48 Hrs. | 72 Hrs. |
| 1 | 64 | 88 | 92 |
| 2 | 76 | 92 | 92 |
| 3 | 72 | 92 | 96 |
| 4 | 20 | 76 | 88 |
| Imidan 50WP - Control | 100 | 100 | 100 |

All of the Imidan concentrates of this invention evaluated here produced high housefly mortalities and were approximately equal in efficacy to commercial Imidan 50WP against houseflies.

EXAMPLE II

Another group of Imidan concentrates of the invention was prepared having the compositions shown in Table III.

TABLE III

| COMPOSITION OF IMIDAN CONCENTRATES, WT % | | | | |
|---|---|---|---|---|
| Components[1] | 5 | 6 | 7 | 8 |
| Polymer-1 | 8.90 | | | |
| Polymer-2 | | 4.70 | | |
| Polymer-3 | | | 4.70 | |
| Polymer-4 | | | | 4.64 |
| Surfactant-1 | 3.60 | | | |
| Surfactant-2 | | | | 4.18 |
| Surfactant-3 | | 2.96 | 2.96 | |
| Solvent-1 | 59.00 | | | |
| Solvent-2 | | 47.02 | | 46.43 |
| Solvent-3 | | | 47.02 | |
| Imidan 50 WP | 28.50 | 45.32 | 45.32 | 44.75 |

[1]Components are described below.
COMPONENTS
Polymer 1 Vinyl Acetate: 2 Ethylhexyl Acrylate (50:50) copolymer prepared in xylene.
Polymer 2 Vinyl Acetate: 2 Ethylhexyl Acrylate (50:50) copolymer prepared in cyclohexane.
Polymer 3 Styrene homopolymer prepared in Mineral Spirits.
Polymer 4 Styrene: 2 Ethylhexyl Acrylate (48:52) copolymer prepared in xylene.
Surfactant 1-Igepal CO 730.
Surfactant 2-Igepal CO 630.
Surfactant 3-Siponic L3.
Solvent 1-Kerosene
Solvent 2-Kwik-Dri
Solvent 3-Mineral Spirits These concentrates and wettable powder Imidan were diluted with water to provide the required Imidan concentration and their insecticidal effectiveness was evaluated before and after rainfall with the several bioassays described above.

Samples 5, 6 and 7 were evaluated with the housefly bioassay. The results are shown in Table IV

TABLE IV

| Sample | Condition | % Housefly Mortality[1] |
|---|---|---|
| 5 | No Rain | 59 |
| 6 | No Rain | 64 |
| 7 | No Rain | 60 |
| Imidan 50 WP | No Rain | 40 |
| 5 | 1 in. Rain | 40 |
| 6 | 1 in. Rain | 46 |
| 7 | 1 in. Rain | 44 |
| Imidan 50 WP | 1 in. Rain | 29 |

[1]At 0.015% concentration.

These data show that the compositions of this invention provided higher housefly mortality than did Imidan 50 WP both before and after rainfall stress.

Sample 8 was compared with wettable powder Imidan in the Mexican bean beetle bioassay before and after a simulated

TABLE V

| BIOASSAY OF IMIDAN COMPOSITIONS | | |
|---|---|---|
| Sample | Condition | % Mortality of MBB[1,2] |
| 8 | No Rain | 80 |
| 8 | 1 in. Rain | 57 |
| Imidan 50WP | No Rain | 64 |
| Imidan 50WP | 1 in. Rain | 26 |

[1]MBB-Mexican Bean Beetle.
[2]At 0.003% concentration.

Again, these data show the insecticidal superiority of the composition of the invention over commerical Imidan 50 WP before and after rainfall.

Samples 6 and 8 and Imidan 50 WP were evaluated in the tobacco budworm bioassay after a 1" simulated rainfall. The results are shown in Table VI.

TABLE VI

BIOASSAY OF IMIDAN COMPOSITIONS

| Sample | % Mortality of Tobacco Budworm[1] 1 lb./acre[2] | 2 lb./acre |
|---|---|---|
| 6 | 80 | 80 |
| 8 | 100 | 60 |
| Imidan 50 WP | 0 | 0 |

[1]After 1 in. of rainfall
[2]In 80 gallons of water

In this evaluation, the wettable powder Imidan showed no efficacy against the tobacco budworm following a rainfall while compositions of the present invention showed a significant degree of control.

EXAMPLE III

A dispersion test was developed and utilized to evaluate the degree of dispersibility and settling of these insecticidal compositions since the better the insecticide is dispersed in the carrier the more uniformly it will be applied to the substrate.

The samples were dispersed in distilled water at a concentration corresponding to that used in the field. The dispersions were moderately shaken and let sit idle for one minute. The aqueous layer above the residue was then removed. A small quantity of distilled water was added to the container to redisperse the residue, and the dispersion was filtered through Whatman No. 4 filter paper. After drying to remove water, the residue was weighed. The larger the amount of residue obtained, the poorer the degree of dispersability of the insecticidal composition.

The results are presented in Table VII.

TABLE VII

DISPERSION TEST OF IMIDAN COMPOSITIONS

| Sample | Wt. Solids Residue |
|---|---|
| 5 | 0.18 |
| 6 | 0.86 |
| 7 | 0.86 |
| 8 | 0.00 |
| Imidan 50 WP | 2.43 |

These data demonstrate that all of the samples containing the compositions of their invention exhibited a higher degree of dispersion than wettable powder Imidan.

What is claimed is:

1. A controlled release dual-mode insecticide composition effective against insects as a contact or stomach poison in the form of an emulsifiable concentrate which comprises:

(a) about 1 to about 40% of Imidan, (b) an amount of film-forming resin effective to controllably release said Imidan comprising about 1 to about 30% of a polymer selected from the group consisting of acrylic resins having an acrylic/acrylate monomer content of about 30 to about 100 weight % of said polymer and styrene homopolymers, (c) about 1 to about 10% of a cationic, anionic or nonionic surfactant, (d) an aliphatic organic solvent in which the resin and the surfactant are substantially soluble but the Imidan is substantially insoluble wherein the weight ratio of the solvent to resin is from 1:1 to 10:1.

2. An insecticide composition according to claim 1 wherein the acrylic resin is a copolymer of vinyl acetate and 2-ethylhexyl acrylate.

3. An insecticide composition according to claim 1 wherein the acrylic resin is a copolymer of styrene and 2-ethylhexyl acrylate.

4. An insecticide composition according to claim 1 wherein the styrene resin is a homopolymer of styrene.

5. An insecticide composition according to claim 1 wherein the aliphatic organic solvent is hexane, heptane, or octane and mixtures thereof.

6. An insecticide composition according to claim 1 wherein the aliphatic organic solvent is mineral spirits, petroleum naphtha containing essentially no aromatic compounds and kerosene.

7. An insecticide composition according to claim 1 wherein the surfactant is aromatic sulfonate-oxide condensates or alkylphenoxypoly (ethyleneoxy) ethanols.

8. A method of controlling foliage eating or chewing insects susceptible to stomach poisons and insects susceptible to contact poisons which comprises:

applying to a foliar substrate the insecticide composition of claim 1.

9. A method of controlling foliage eating or chewing insects susceptible to stomach poisons and insects susceptible to contact poisons which comprises:

applying to a foliar substrate the insecticide composition of claims 2, 3, 4, 5, 6 or 7.

* * * * *